United States Patent [19]
Keiter

[11] Patent Number: 5,178,019
[45] Date of Patent: Jan. 12, 1993

[54] HEATED LIQUID SAMPLING PROBE FOR AN AUTOMATED SAMPLING APPARATUS

[75] Inventor: Dean Keiter, Durham, N.C.

[73] Assignee: Akzo N.V., Arnhem, Netherlands

[21] Appl. No.: 674,957

[22] Filed: Mar. 26, 1991

[51] Int. Cl.$^5$ ............................................. G01N 1/14
[52] U.S. Cl. ................................. 73/863.11; 73/864.24
[58] Field of Search ........... 73/863.11, 863.12, 864.73, 73/864.74, 864.24, 864.25

[56] References Cited

U.S. PATENT DOCUMENTS

| | | | |
|---|---|---|---|
| 3,774,237 | 11/1973 | Hardway, Jr. | 73/304 C X |
| 3,967,168 | 6/1976 | Christensen | 361/323 |
| 4,170,311 | 10/1979 | Spaw | 73/290 V X |
| 4,302,965 | 12/1981 | Johnson et al. | 73/55 |
| 4,356,733 | 11/1982 | Braunweiler | 73/863.11 |
| 4,736,638 | 4/1988 | Okawa et al. | 73/864.24 |
| 4,756,200 | 7/1988 | Ramsner et al. | 73/863.11 |
| 4,822,331 | 4/1989 | Taylor | 494/16 |
| 4,829,837 | 5/1989 | Telfer | 73/863.01 |
| 5,027,075 | 6/1991 | Harding, Jr. | 73/864.24 X |
| 5,049,826 | 9/1991 | Sasao | 73/864.24 X |

*Primary Examiner*—Tom Noland
*Attorney, Agent, or Firm*—Spencer, Frank & Schneider

[57] ABSTRACT

A heated liquid sampling probe for an automated sampling apparatus includes a sampling tube for drawing up a volume of liquid. The tube is connectable to an automated sampling apparatus including a chassis. A capacitance exists between the sampling tube and the chassis. An electrical heater is arranged for heating the tube and a volume of liquid contained therein. The electrical heater increases the capacitance between the tube and the chassis. A capacitance lowering mechanism is provided for lowering the increase in capacitance due to the heater.

16 Claims, 4 Drawing Sheets

HEATED LIQUID SAMPLING PROBE FOR AN AUTOMATED SAMPLING APPARATUS

CROSS-REFERENCE TO RELATED APPLICATIONS

This application is related to copending U.S. patent application Ser. No. 07/443,951, filed Dec. 1st, 1989, entitled "Sample Handling System For An Optical Monitoring System," which is owned by the Assignee of the present application, and the disclosure of which is incorporated herein by reference. Ser. No. 07/443,951 has been abandoned. However, a continuation-in-part application thereof, Ser. No. 07/883,950, was filed on Feb. 11, 1992.

BACKGROUND OF THE INVENTION

The present invention relates to an automated sample handling system having a heated liquid sampling probe.

Automated sample handling systems are known which automatically dispense fluid samples, such as blood plasma and reagents, into the reaction well of a cuvette. Such instruments are useful in the field of biochemical analysis for measuring blood clotting times and for automatically carrying out other bioassays.

An automated sample handling system of this type is described in U.S. patent application Ser. No. 07/443,951. In this system a temperature controlled housing is provided for storing the fluid samples and reagents at a relatively cool temperature for preventing degradation of the samples and reagents prior to sample analysis. The temperature controlled housing typically maintains the fluid samples and reagents at a temperature of 4° C. The actual analyses are generally carried-out at 37° C. (98.6° F.), standard human body temperature. Accordingly, it is necessary to heat up the fluid sample and reagents to 37° C. prior to analysis.

In the above-described sample handling system, a temperature-controlled linear track on which the cuvettes are transported is sufficient to bring the fluid samples to the reaction temperature. However, it has been found necessary to pre-heat the reagents while in the sampling tube prior to being dispensed in the reaction well of a cuvette in order to assure the reaction volume is at the proper temperature at the proper time.

In order to achieve the desired heating of a volume of liquid in the liquid sampling tube, it has been attempted to use an electric heating element disposed directly on the tube. These attempts have failed because previous applications of electrical heating elements placed directly against the sampling tube have caused malfunctions in the capacitive touch liquid level sensing devices commonly used with automated liquid sample handling systems.

One of those known attempts to heat the sampling tube and the aspirated liquid therein by an electric heater element was abandoned owing to unsatisfactorily results. The results were unsatisfactory because the electrical heater increased the capacitance developed between the liquid sampling tube and the instrument chassis to such a large extent that the capacitive touch liquid level sensing device or, simply, the capacitance measuring device, was unable to accurately detect the change in capacitance when the sampling tube contacted the surface of the liquid to be sampled. Thus, for example, a robotic arm controlled by information from the capacitance measuring device failed to stop lowering a sampling tube into a liquid sample as the capacitance measuring device was unable to detect the surface of the liquid to be sampled and, hence, was unable to send such information to a central controller for operating the robotic arm.

To understand why those known attempts at using an electrical heating element disposed directly on the liquid sampling tube failed, a discussion of how the capacitance measuring device functions, as applied in this environment, follows.

Basically, in this environment the capacitive liquid level sensor works on the principle of measuring the change in capacitance between the sampling tube and the chassis of the instrument. The sampling tube forms one "plate" and the chassis forms the other "plate" of the capacitor. Atmospheric air is the dielectric. When the liquid sampling tube touches the surface of the liquid to be sampled, the plate of the capacitor that is formed by the sampling tube is now effectively larger because of its contact with the liquid sample. This increases the capacitance between the sampling tube and the chassis that is detected by the liquid level sensing device.

This change in capacitance indicates that the liquid sampling tube has contacted the surface of the fluid sample and this information is sent to the central controller of the instrument for sending control signals to the robotic arm. The control signals tell the robotic arm how much further past the detected surface to lower the fluid sampling tube into the liquid sample for aspirating a predetermined amount of fluid to be analyzed. A known capacitive touch liquid level sensor is supplied by CAVRO Scientific Instruments, Inc., Sunnyvale, Calif., and marketed as Model No. 721014B. The control signals for controlling the robotic arm are received and sent by the central controller of the instrument in a manner well understood by those skilled in the art.

A further attempt to solve the problem of heating a sampling tube without adversely affecting the capacitive touch liquid level sensor is known. In this attempt a water jacket was disposed on the liquid sampling tube for circulating warm fluid to heat up the aspirated sample. However, such a water jacket proved to be unsatisfactory owing to its being bulky, and, hence, not usable in the desired application with an automated liquid sampling apparatus.

SUMMARY OF THE INVENTION

It is therefore an object of the invention to provide a heated sampling probe for a sample handling system that can reliably heat a volume of liquid without adversely affecting the operation of an associated capacitive touch liquid level sensor.

It is a further object of the invention to provide an automatic liquid sample handling system that can handle a high throughput of patient samples by concurrently aspirating and heating a volume of liquid while maintaining a high degree of reliability.

The above and other objects are accomplished according to the invention in the context of a heated liquid sampling probe for an automated sampling apparatus mounted on a chassis, comprising a sampling tube for drawing up a volume of liquid, the tube presenting a capacitance with respect to the chassis. An electrical heater means is arranged for heating the tube and a volume of liquid contained therein. The electrical heater means causes an increase in the capacitance between the sampling tube and the chassis. A capacitance lowering means is arranged for reducing the increase in capacitance caused by the presence of the heater means.

According to a further aspect of the invention, the electrical heater is a length of heating wire coiled around the sampling tube.

According to another aspect of the invention, the capacitance lowering means is a heat-shrinkable insulation tubing disposed on the sampling tube between the tube and the electrical heater.

According to yet another embodiment of the invention, the capacitance lowering means includes an electrical relay which opens the circuit between the heater and the power supply when the capacitive touch liquid level sensor is operating, thus breaking the capacitance path between the tube and the chassis through the heater.

According to a still further aspect of the invention, the electrical relay means comprises a MOSFET transistor (metal oxide semiconductor field effect transistor).

According to another embodiment of the invention, a switching capacitor is used for transferring power between a power supply and the electrical heating element. The switching capacitor stores power supplied by the power supply, while capacitively isolating the tube from the power supply through the heating element during operation of the capacitive touch liquid level sensor. Thereafter, the switching capacitor is switched to be electrically connected to the heating element for transferring the stored power to the heating element for heating the sample probe.

According to a still further embodiment a heating element is disposed on the sampling probe and a power source supplies energy to the heater element. A transformer having a primary winding and a secondary winding with low capacitance between the primary and secondary windings is provided with the secondary winding being connected to the heating element. A pulse modulation means is connected between the power source and the primary winding for pulse modulating a current supplied to the primary winding from the power source.

Other details and advantageous features of the invention will become apparent from the following description when taken in connection with the accompanying drawings and the appended claims.

DETAILED DESCRIPTION OF THE PREFERRED EMBODIMENTS

Figure 1:
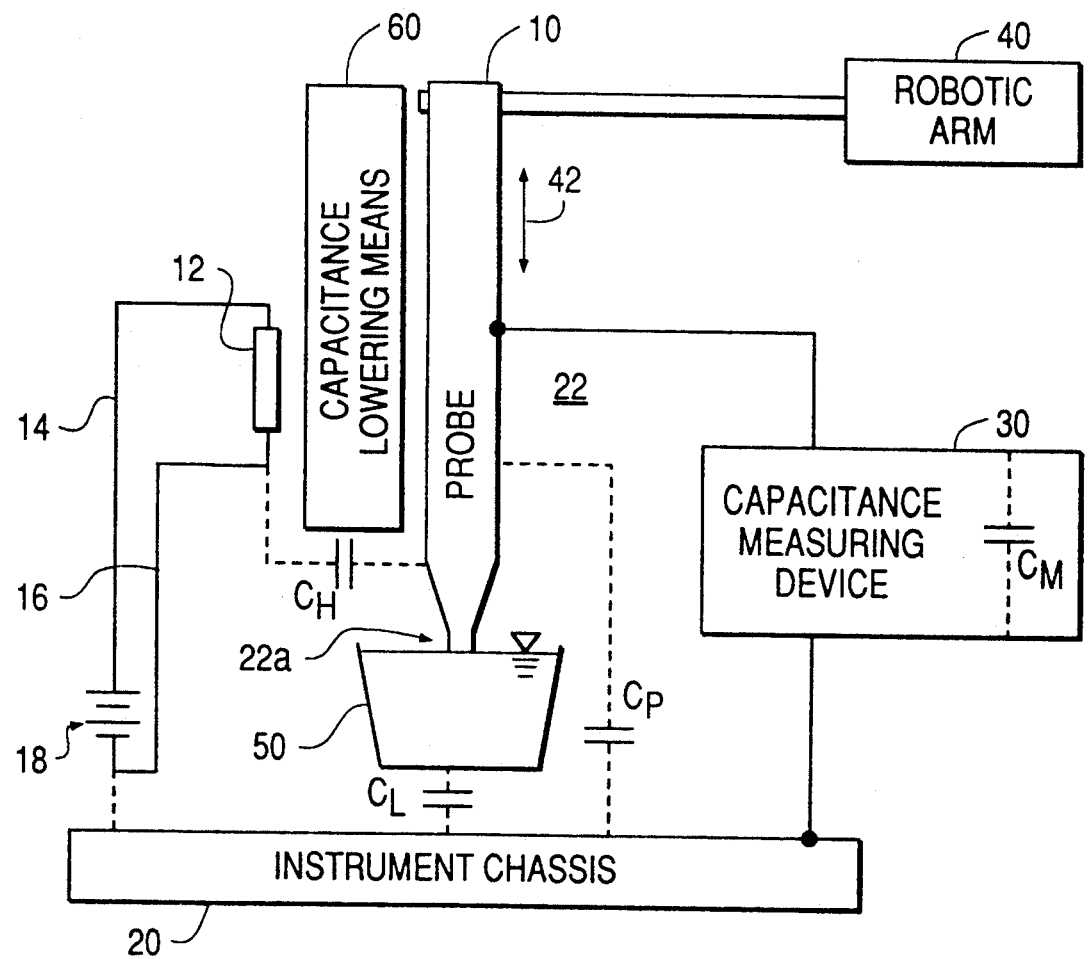
FIG. 1 is an electrical schematic of one embodiment of a heating mechanism for a sample handling probe according to the invention.

Referring to FIG. 1, there is schematically shown an automated sampling apparatus having a heated liquid sampling probe 10 according to the invention. A robotic arm 40 maneuvers probe 10 between reagent containers, such as reservoir 50, to a reaction cuvette (not shown) for automatically aspirating and dispensing reagents as described, for example in U.S. patent application No. 07/443,951. Thus, robotic arm 40 can raise and lower probe 10 in the direction of arrow 42 for taking a volume of liquid from liquid reservoir 50. Probe 10 includes a metallic tube 22 having a narrow tip 22a for dipping into reservoir 50 and aspirating a measured amount of reagent. As previously discussed, in certain applications it is desirable to heat the reagent in the probe while the probe is being moved by the robotic arm toward the cuvette where the reagent is dispensed. For this purpose, the probe is provided with a heater 12. Heater 12 preferably comprises a coiled nichrome wire wrapped around tube 22 and is electrically connected by wires 14, 16 to a power supply 18 which shares a common ground with chassis 20. Power supply 18 can be either a DC or AC power supply.

In order to aspirate a measured amount of reagent from reservoir 50, it is necessary to detect when probe 10 contacts the surface of the reagent. As previously discussed, this is typically accomplished with the use of a capacitance measuring device 30 which detects a change in capacitance between tube 22 and chassis 20 when the tube contacts the reagent in reservoir 50. Tube 22 presents a first capacitance $C_P$ relative to chassis 20. Heater 12, which has a common ground with instrument chassis 20 and capacitively is part of the chassis, presents a second capacitance $C_H$ with reference to tube 22. Liquid reservoir 50 presents an additional capacitance $C_L$ with respect to chassis 20 when probe 10 contacts the liquid. Capacitance measuring device 30 measures the capacitance $C_M$ which is presented between the liquid sampling probe 10 and the instrument chassis 20 where $C_M = C_P + C_L + C_H$. Detection of the additional capacitance $C_L$ by capacitance measuring device 30 indicates when probe 10 contacts the liquid in container 50. The presence of capacitance $C_H$ introduced by heater 12, however, can mask the ability of capacitance measuring device 30 to sense the changes in $C_M$ by the amount $C_L$. The present invention provides a mechanism for lowering capacitance $C_H$ to the point where capacitance measuring device 30 can sense the change $C_L$ in capacitance $C_M$. In the embodiment shown in FIG. 1 this is accomplished by providing an insulation 60 between the heater 12 and tube 22 which has been found to lower capacitance $C_H$.

Figure 2:
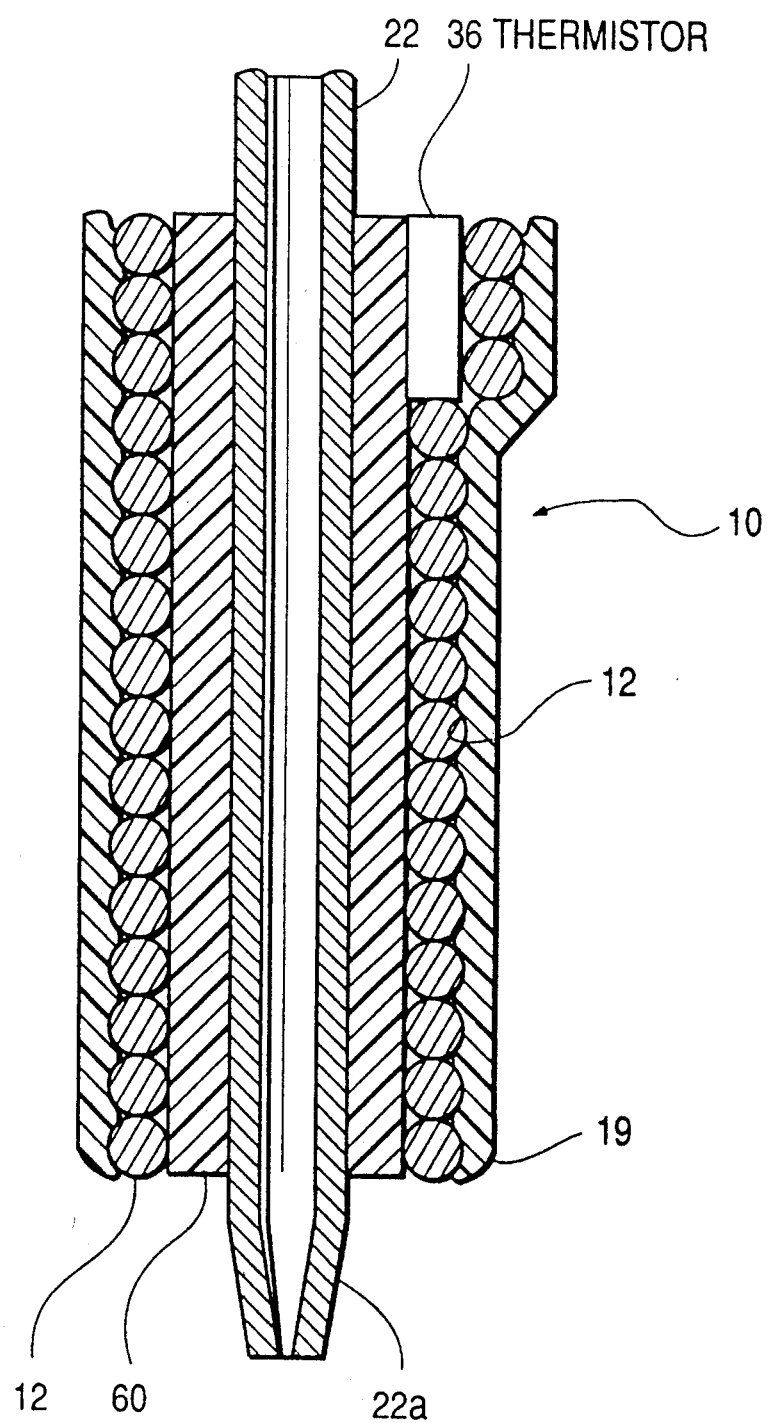
FIG. 2 is a schematic sectional side view of a heated sampling probe having a capacitance lowering member according to the invention.

Referring to FIG. 2, there is shown an enlarged view of the heated liquid sampling probe 10 shown in FIG. 1. The principal elements of the heated liquid sampling probe 10 include the elongated sampling tube 22, which is generally a metallic tube, such as a stainless steel needle. Heater 12, which is preferably a heating coil of nichrome wire wrapped around sampling probe 10, heats sampling tube 22 and a volume of liquid held therein. Insulating material in the form of heat-shrinkable tubing 60, is disposed between sampling tube 22 and the heating device 12.

The heat-shrinkable tubing 60 reduces the increase in capacitance caused by the presence of the heater 12. The disposition and operation of tubing 60 and other embodiments of the capacitance lowering means will be even clearer from the description of the operation of the invention as described below. Preferably, an adhesive 19 surrounds the heater 12 for rigidifying and holding together the various elements. A thermistor 36 is provided adjacent to heater 12 for monitoring the temperature so that the liquid sample aspirated by sampling tube 22 can be accurately heated.

The operation of the automated sampling apparatus having the heated liquid sampling probe will now be described in the context of a specific example of the invention used in experimental text runs, it being understood that the invention is not limited to this particular example.

In the test run configuration probe 10 included a stainless steel needle or sampling tube 22 around which a 73.5 inch (1870 mm) long piece of enamel-coated nichrome-60 type wire was coiled as heater 12. The enamel-coated nichrome-60 wire was a 32 gauge wire as measured without the enamel coating. The experimental length of nichrome-60 wire gave a 64 Ω resistance, and was wrapped around sampling tube 22 about 100 times in a single layer. Heat-shrinkable tubing was disposed between sampling tube 22 and the coiled nichrome-60 wire, the heat-shrinkable tubing functioning as capacitance lowering means 60 and being made of a polyolefin tube 0.014 in (0.36 mm) thick, having a diameter of 3/32 in (2.4 mm). The sampling tube 22 was coated on the inside with polytetrafluoroethylene and had an outer diameter of 0.073 inch (1.85 mm).

Thermistor 36 used to monitor the temperature during the test run, was supplied by Thermometrics, Inc., Model No. MA 100DD-103-B, and had stated operating characteristics of 10 kΩ@25° C.±0.1° C. Further, the capacitance measuring device 30 was a CAVRO Scientific Instruments, Inc. Model No. 721014B liquid level sensor. The nichrome wire heating element 12 was powered by a 10 volt power supply.

Tests were first run with heating element 12 disposed on tube 22 without the capacitance lowering means 60 of the invention. In those tests, $C_H$ was measured as 45 pF both when the probe was above and in contact with the surface of the liquid; $C_p$ was measured to be 50 pF in both instances; and $C_L$ was always 10 pF. Thus $C_M$ was calculated to be 95 pF when the probe was above the liquid surface (i.e., $C_M=C_H+C_p=45+50=95$) and $C_M$ was calculated to be 105 pF when contacting the liquid surface (i.e., $C_M=C_L+C_H+C_p=10+45+50=105$). The difference between 95 pF and 105 pF, however, was insufficient to allow capacitance measuring device 30 to detect the change in capacitance, and, hence, the robotic arm failed to halt the downward movement of probe 10 into the volume of liquid, as the capacitance measuring device failed to register a change in capacitance sufficiently great to send appropriate signals to the control unit.

When the heat-shrinkable tubing 60 according to the invention functioning as the capacitance lowering means was disposed between heating element 12 and tubing 22, the measured value for $C_H$ was 25 pF both when probe 10 was above and at the liquid surface; and, $C_p$ was likewise 50 pF in both instances. Accordingly, the capacitance $C_M$ was found to be 75 pF ($C_M=C_H+C_p=25+50=75$), and 85 pF ($C_M=C_L+C_H+C_p=10+25+50=85$), when the probe was above and at the liquid surface, respectively. This greater difference in the relative change of the measured capacitance was sufficiently large to allow the capacitive touch liquid level sensor 30 to detect the change in capacitance between the probe and the chassis and thus to indicate when the probe contacted the liquid surface.

Figure 3:
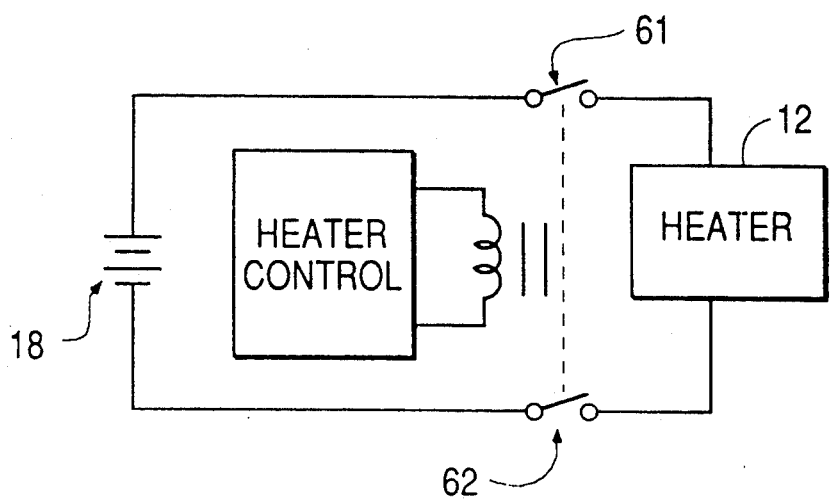
FIG. 3 is an electrical schematic of a heating mechanism for a sampling probe with a capacitance lowering device according to another embodiment of the invention.

Further embodiments of capacitance lowering means according to the invention are shown in FIGS. 3 to 6. Referring to FIG. 3, electromechanical relays 61, 62 are used as an alternative to the heat-shrinkable tubing 60 for lowering capacitance $C_H$. Relays 61,62 are located in series with power supply 18 and heating element 12. In the open-circuit condition shown in FIG. 3, relays 61, 62 electrically isolate heating element 12 from power supply 18, and, hence, the capacitance path between the tube 22 and instrument chassis 20 is broken. In this embodiment, tube 22 is obviously not heated by heating element 12 while tube 22 is lowered into the liquid and capacitance measuring means 30 is operated. Switches 61, 62 are closed and heater 12 is operative for heating tube 22 only after the tube is withdrawn from the liquid reservoir.

Figure 4:
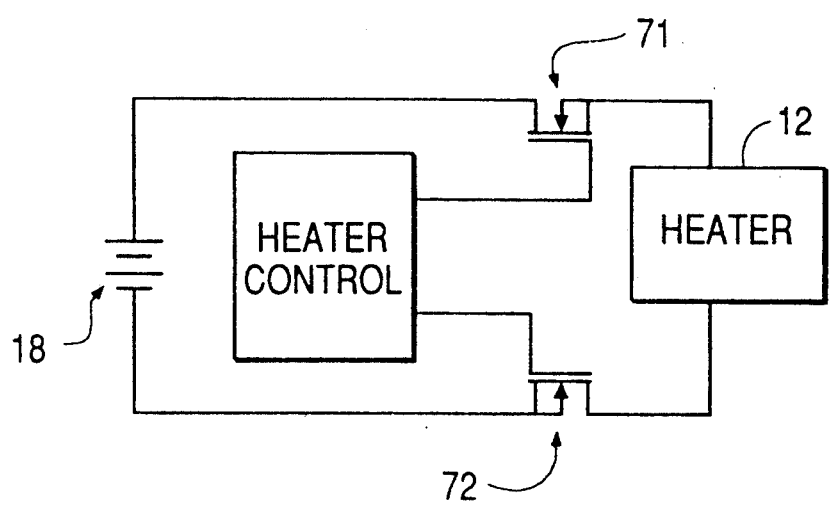
FIG. 4 is a schematic view similar to FIG. 3 of another embodiment of the invention.

In FIG. 4 a still further embodiment of the invention is schematically shown in which MOSFET transistors 71, 72 are used in place of relays 61, 62 of the embodiment of FIG. 3. The operation of the embodiment of FIG. 4 is similar to the operation of the embodiment of FIG. 3.

Figure 5:
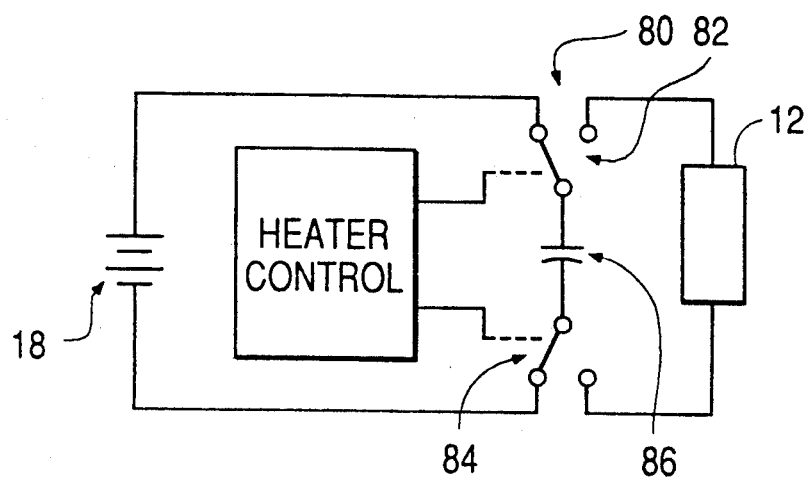
FIG. 5 is a schematic view similar to FIG. 3 of a still further embodiment of the invention.

In FIG. 5, a switching capacitor circuit 80 is used for transferring power between power supply 18 and electrical heater 12 by way of relays 82, 84. In a first state, switching relays 82, 84 connect a capacitor 86 in series with power supply 18 thus charging capacitor 86. In this state, the capacitance path between the sampling tube and the power source (chassis) through the heater is broken and capacitance measuring device may be effectively operated for sensing when tube 22 contacts the liquid. When heating element 12 is to be heated, switching relays 82,84 are moved to a second state in which switching relays 84,86 connect capacitor 86 in series with heating element 12, whereby capacitor 86 discharges through heater 14.

Figure 6:
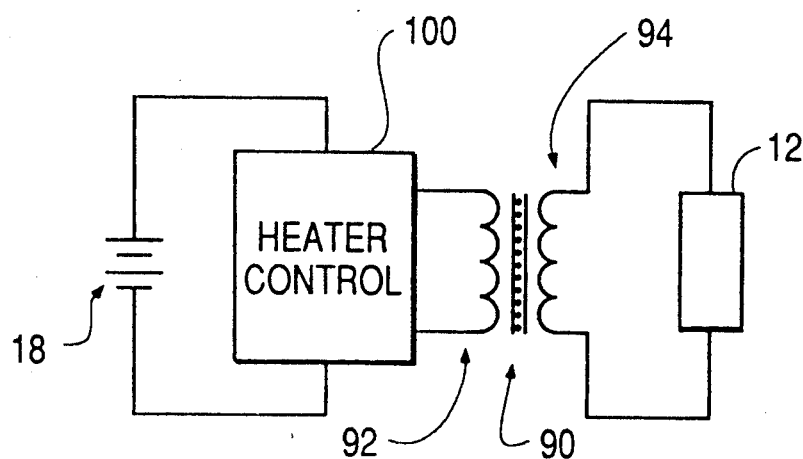
FIG. 6 is a schematic view similar to FIG. 3 of yet another embodiment of the invention.

In FIG. 6, heating element 12 is electrically connected to power supply 18 by way of a transformer 90. Transformer 90 has a primary winding 92 and a secondary winding 94 with low capacitance between the primary and secondary windings. A heater control 100 in the form of a pulse modulation device is connected in series between power supply 18 and primary winding 92 for pulse modulating a current supplied to primary winding 92. The secondary winding 94 is electrically connected in series with heating element 12.

It will be understood that the above description of the present invention is susceptible to various modifications, changes and adaptations, and the same are intended to be comprehended within the meaning and range of equivalents of the appended claims.

What is claimed:

1. A heated liquid sampling probe for an automated sampling apparatus mounted on a chassis, comprising:
   a sampling tube for drawing up a volume of liquid, said tube presenting a capacitance with respect to the chassis;
   electrical means disposed on said tube for heating said tube and the volume of liquid contained therein, said electrical heat means causing an increase in the capacitance between said tube and the chassis; and
   capacitance lowering means disposed for reducing the increase in capacitance caused by the presence of said electrical heating means.

2. A probe as defined in claim 1, wherein said heater means comprises a length of heating wire coiled around said tube.

3. A probe as defined in claim 1, wherein said tube is metallic.

4. A probe as defined in claim 1, wherein said capacitance lowering means comprises heat-shrinkable insulation tubing disposed on said tube between said tube and said electrical heater means.

5. A probe as defined in claim 1, wherein said capacitance lowering means includes switching means for breaking a capacitance path between said sampling tube and the chassis through said heater means.

6. An apparatus as defined in claim 5, wherein said switching means comprises electromechanical relays.

7. An apparatus as defined in claim 5, wherein said switching means includes MOSFET transistors.

8. A probe as defined in claim 1, and further including a power source for supplying energy to said electrical heater means; wherein said capacitance lowering means includes a transformer having a primary winding and a secondary winding, and pulse modulation means connected between said power source and said primary winding for pulse modulating a current supplied to said primary winding from said power source, said secondary winding being connected to said heater means.

9. A liquid sampling probe for obtaining and heating a liquid sample, comprising:

a chassis;

a liquid sampling tube attached for relative movement with respect to said chassis for dipping said tube into a container of liquid to be sampled, said tube presenting a capacitance relative to said chassis;

capacitance measuring means connected between said chassis and said tube for detecting when said tube touches the surface of the liquid to be sampled by detecting a change in capacitance between said tube and said chassis when said tube is free of contact with the surface of the liquid to be sampled and when said tube is in contact with the surface of the liquid to be sampled;

heater means disposed on said tube for heating a liquid sample received in said tube, the presence of said heater means causing an increase in the capacitance between said tube and said chassis; and capacitance lowering means for sufficiently lowering the increase in capacitance caused by the presence of said heater means to enable said capacitance measuring means to detect the change in capacitance when said tube contacts the surface of the liquid in the container.

10. An apparatus as defined in claim 9, wherein said heater means comprises a length of heating wire coiled around said tube.

11. An apparatus as defined in claim 9, wherein said tube is metallic.

12. An apparatus as defined in claim 9, wherein said capacitance lowering means comprises heat-shrinkable, insulation tubing disposed on said tube between said tube and said electrical heater means.

13. A probe as defined in claim 9, wherein said capacitance lowering means includes switching means for breaking a capacitance path between said sampling tube and the chassis through said heater means.

14. An apparatus as defined in claim 13, wherein said switching means comprises electromechanical relays.

15. An apparatus as defined in claim 13, wherein said switching means includes MOSFET transistors.

16. A probe as defined in claim 9, and further including a power source for supplying energy to said electrical heater means; wherein said capacitance lowering means includes a transformer having a primary winding and a secondary winding, and pulse modulation means connected between said power source and said primary winding for pulse modulating a current supplied to said primary winding from said power source, said secondary winding being connected to said heater means.

* * * * *